United States Patent
Hsu et al.

(10) Patent No.: US 10,500,419 B2
(45) Date of Patent: Dec. 10, 2019

(54) RADIATION SHIELDS FOR LINAC HEAD AND SYSTEM

(71) Applicant: Varian Medical Systems, Inc., Palo Alto, CA (US)

(72) Inventors: HsinLu Hsu, Sunnyvale, CA (US); Magdalena Constantin, Los Altos, CA (US); Stuart Scollay, San Jose, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 16/401,061

(22) Filed: May 1, 2019

(65) Prior Publication Data

US 2019/0255360 A1  Aug. 22, 2019

Related U.S. Application Data

(62) Division of application No. 14/851,646, filed on Sep. 11, 2015, now Pat. No. 10,322,300.

(51) Int. Cl.
*A61N 5/10* (2006.01)
*G21G 4/08* (2006.01)
*G21F 3/00* (2006.01)
*G06F 17/50* (2006.01)

(52) U.S. Cl.
CPC ............ *A61N 5/1077* (2013.01); *G21F 3/00* (2013.01); *G21G 4/08* (2013.01); *A61N 2005/1094* (2013.01); *G06F 17/50* (2013.01)

(58) Field of Classification Search
CPC .......... A61N 5/1077; A61N 2005/1094; G21F 3/00; G21G 4/08; A61B 6/107; A61B 6/44; G06F 17/50
See application file for complete search history.

(56) References Cited

U.S. PATENT DOCUMENTS

| | | | |
|---|---|---|---|
| 7,758,241 B2 * | 7/2010 | Sliski ....................... | A61N 5/10 250/505.1 |
| 2011/0198516 A1 * | 8/2011 | Fan ......................... | G21F 1/125 250/518.1 |
| 2015/0100290 A1 * | 4/2015 | Falt ....................... | A61N 5/1075 703/2 |
| 2017/0309355 A1 * | 10/2017 | Lee ........................ | G21F 1/085 |

* cited by examiner

*Primary Examiner* — Brooke Purinton
(74) *Attorney, Agent, or Firm* — IP Legal, Varian Medical Systems, Inc.

(57) ABSTRACT

In a method of constructing a head shield for a radiation machine, the angular distribution of radiation propagating from a source and the angular function of thickness of a material in attenuating the radiation to a certain level of its original value are determined. Based on the angular distribution of radiation from the source and the angular function of thickness of the material, the thicknesses of the material at a plurality of angular locations around the source and distances from the source can be calculated for attenuating the radiation to or less than a predetermined threshold value. A shield around the source is constructed based on the calculated thicknesses of the material through iterative steps to ensure a cost-saving, weight-efficient, optimal solution. A method of designing a local radiation shield for a point of interest in a radiation system is also described to improve the machine reliability, regardless of the motion component of the POI with respect to the main radiation source and the secondary radiation source created by the patient scatter.

28 Claims, 12 Drawing Sheets

RADIATION SHIELDS FOR LINAC HEAD AND SYSTEM

CROSS REFERENCE TO RELATED APPLICATIONS

This application is a division of U.S. Ser. No. 14/851,646 filed Sep. 11, 2015 entitled "RADIATION SHIELDS FOR LINAC HEAD AND SYSTEM," the disclosure of which is incorporated herein by reference in its entirety.

TECHNICAL FIELD

Embodiments of this disclosure relate generally to radiation apparatuses and methods. In particular, various embodiments of methods of designing radiation shields for radiation machines and systems are described.

BACKGROUND

Medical linear accelerators (LINACs) are useful in producing high energy radiation to treat patients with cancer. Depending on the type of cancer, position, size of the tumor and its surrounding critical organs, and the patient size, medical LINACs operating at energies from ~4 to ~20 MeV range are used for radiation therapy procedures. To ensure safety however, protective measures must be taken to limit unwanted radiation to patients outside the planned treatment field and to radiotherapists and the general public to an acceptable level. Electronic components sensitive to radiation exposure in the system also need to be protected from excessive radiation to prolong their useful life span.

Radiation in directions other than the direction toward the intended places, such as tumor, is undesirable. Hence proper shielding is required. Unwanted radiation is called radiation leakage which in general have three major aspects: (1) Leakage to patients. This results in higher risk of patients getting secondary cancers, hence the lower the better. (2) Leakage to general public. Linac leakage to the operators or others is shielded by the treatment room. Reduced leakage can result in lower cost of the treatment room. (3) Leakage to the linac system itself. There are many PCBs and components located inside the treatment room and many of their performance degrade over time due to radiation damage. Reduced leakage to these parts can reduce the maintenance resource and service cost. Because of above, a well-designed shielded system is very important. Conventionally, machine shielding is developed based on a trial-and-error approach, which requires costly schedules, budgets and resources, and results in heavy and costly shielding parts and assembly. Furthermore, machine leakage performances are unknown until prototypes are constructed and actual measurements are made. In addition, unintended leakage hot spots may exist, incurring more expensive room shielding and short life span of electronic machine components. This application describes a systematic method to design and optimize the shielding that reduces the cost of the shielding itself and overall cost in above aspects.

SUMMARY

Embodiments of methods for designing LINAC head shields and LINAC system shields are described. Also described are LINAC head shields and system shields constructed using the design methods. Other embodiments are described further herein.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION

Various embodiments of methods for designing LINAC head shields and system shields are described. It is to be understood that the disclosure is not limited to the particular embodiments described as such may, of course, vary. An aspect described in conjunction with a particular embodiment is not necessarily limited to that embodiment and can be practiced in any other embodiments. For instance, various embodiments are presented using LINACs producing x-ray radiation. It will be appreciated that the disclosed methods can be implemented in other types of radiation machines and systems producing other types of radiation such as gamma rays.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. In the following description, well known components or steps may not be described in detail in order to avoid unnecessarily obscuring the embodiments of the disclosure.

Figure 1A:
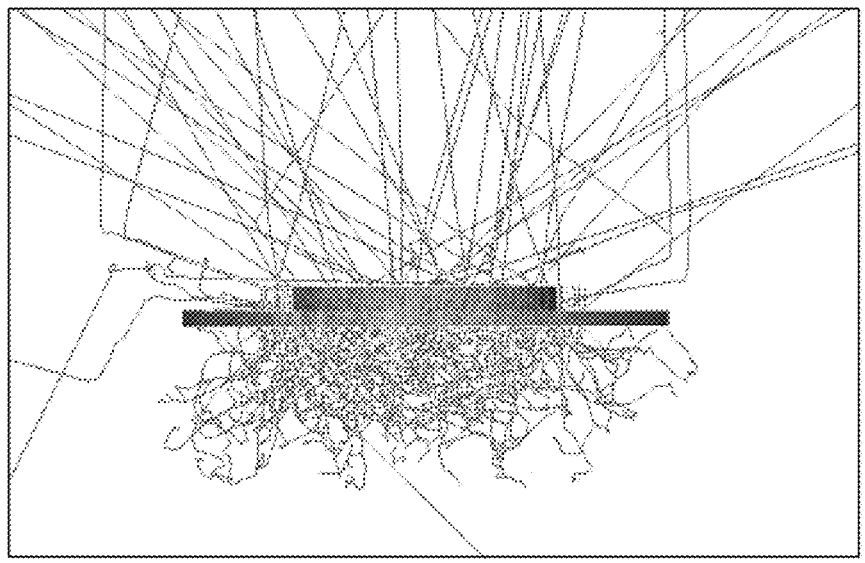
FIG. 1A schematically shows the trajectories of electrons before and after bombarding a target in producing Bremsstrahlung radiation.
Figure 1B:
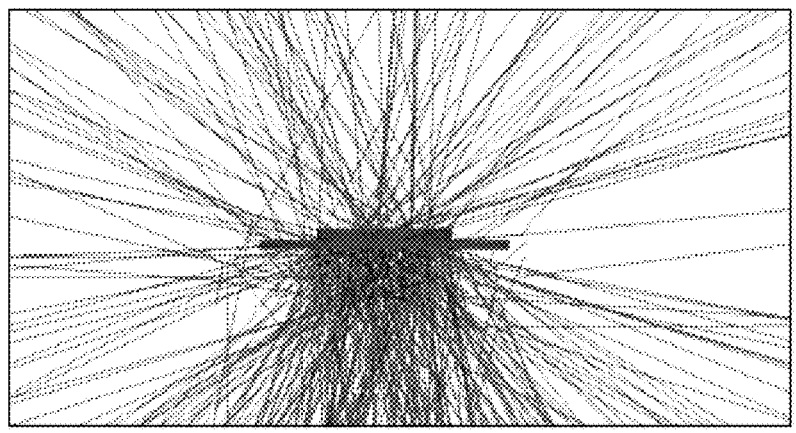
FIG. 1B schematically shows the trajectories of photons produced.
Figure 1C:
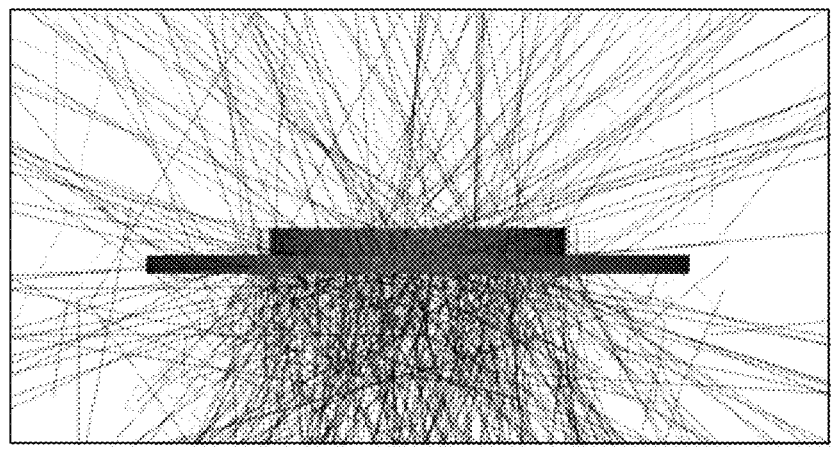
FIG. 1C schematically shows the trajectories of both electrons and photons, combining FIGS. 1A and 1B.

As used herein, the phrase "angular distribution of radiation" refers to a distribution of radiation propagating from a source as a function of spatial angle. By way of example, FIG. 1A schematically shows the trajectories of electrons before and after bombarding a target in producing radiation. FIG. 1B schematically shows the trajectories of photons produced. FIG. 1C schematically shows the trajectories of both electrons and photons, combining FIGS. 1A and 1B. As shown in FIGS. 1A-1C, when energetic electrons are stopped in a target, they generate Bremsstrahlung radiation (photons) which propagates largely in a forward direction. There is a considerable angular spread in the resulting photons. Some photons backscatter, i.e., propagate at 180 degrees with respect to the electron beam direction. The distribution of photons generated is a function of spatial angle, and may be effected by the energy and/or energy spectrum of the electrons striking the target, the geometric configuration of the target, the material composition of the target, and the surrounding target holder. As the TVL changes with angle, it is desirable to provide the disclosed method, as will be described in greater detail below, to design linac shield with minimum material and cost to achieve intended design per leakage specification.

As used herein, the phrase "photon fluence" refers to the number of photons per unit area. The phrase "energy photon fluence" refers to a summation of photon fluence weighted by the corresponding photon energy. The phase "radiation dose" or "dose" refers to absorbed dose or energy deposited per unit mass. In this disclosure, the phrase "angular distribution of radiation dose" may be used interchangeably with the phrase "dose lobe." The phrase "angular distribution of energy photon fluence" may be used interchangeably with the phrase "energy fluence lobe." The phrase "angular distribution of photon fluence" may be used interchangeably with the phrase "photon fluence lobe." In this disclosure, the phrase "angular distribution of radiation" includes angular distribution of photon fluence, angular distribution of energy photon fluence, and/or angular distribution of radiation dose.

In general, less material is needed at large angle due to reduced dose lobe intensity and reduced TVL.

As used herein, the phrase "primary radiation" refers to the portion of radiation emitted directly from a target source that did not suffer any interactions or scattering events with any of the radiation collimation components and is confined to the treatment field. The phrase "secondary radiation" refers to radiation scattering off from objects such as the patient, machine parts including components in the collimation system or radiation shield, and walls of the treatment room etc. Secondary radiation is in general undesirable and can be significant to critical organs near the treatment field and/or to electronic components or devices in the radiation system sensitive to radiation.

As used herein, the phrase "Tenth-Value-Layer" ("TVL") refers to the thickness of a material which, when introduced into the path of a given radiation beam, attenuates the radiation intensity to one-tenth of its original value. By way of example, the first TVL of a material attenuates radiation intensity to one-tenth of its original value, the second TVL attenuates it to one-hundredth, and the third TVL attenuates it to one-thousandth, etc. The phrase "Half-Value-Layer" ("HVL") refers to the thickness of a material which, when introduced into the path of a given radiation beam, attenuates the radiation intensity to one-half of its original value. By way of example, the first HVL of a material reduces radiation intensity to half of its original value, and the second HVL reduces it by a factor of four, etc.

The TVL, HVL or the similar, of a material depends on the attenuating property of the material such as the density and atomic number of the material. In general, high density materials have higher radiation stopping power than lower density materials with the same thickness.

Figure 7:
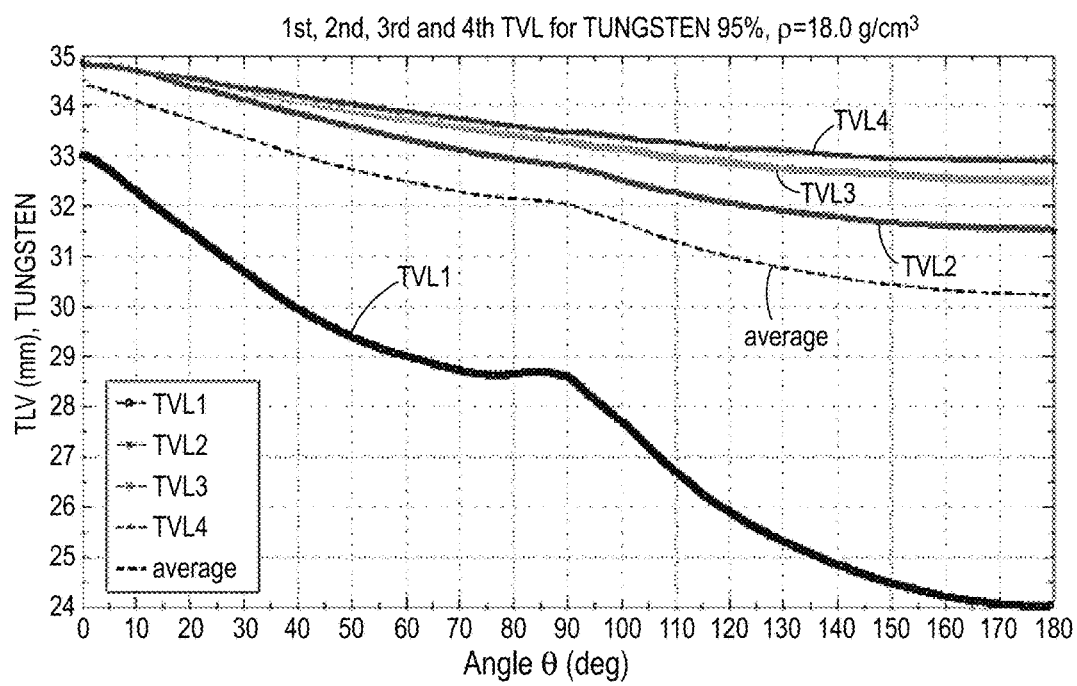
FIG. 7 shows an angular dependence of Tenth-Value-Layers (TVLs) for tungsten according to some embodiments of the disclosure.
Figure 9:
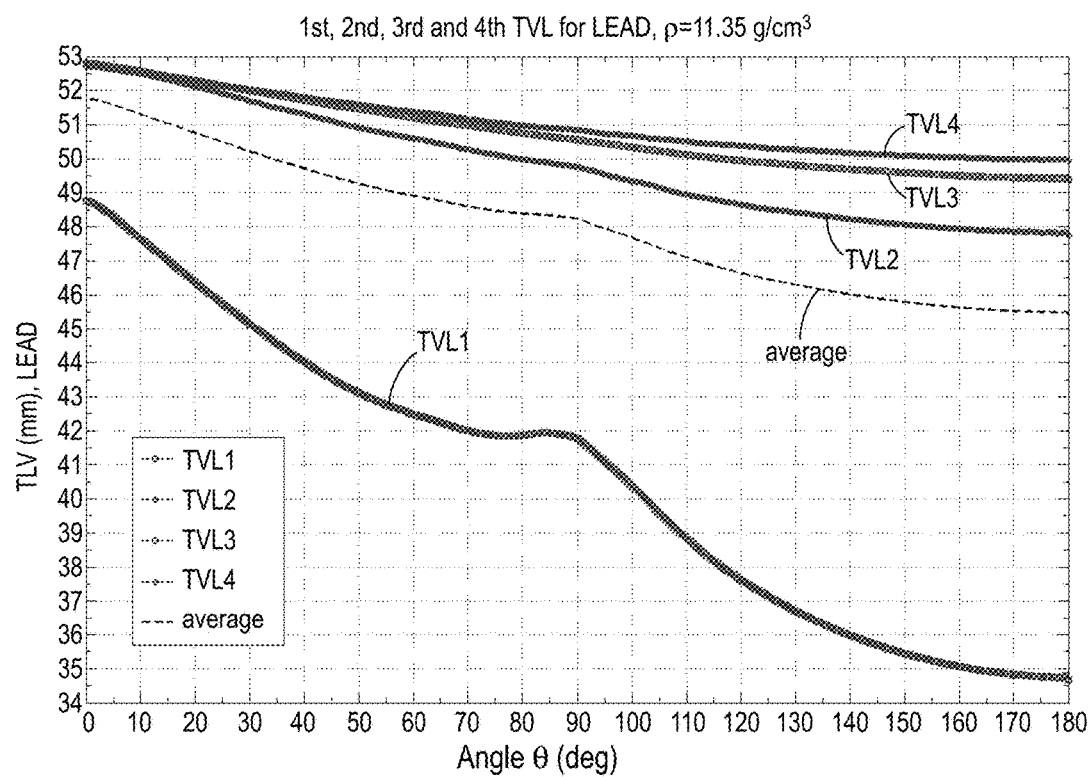
FIG. 9 shows an angular dependence of Tenth-Value-Layers (TVLs) for lead according to some embodiments of the disclosure.

The TVL, HVL or the similar, of a particular material varies depending on the angular location of the material with respect to the source. In general, the TVL, HVL or the similar, of a particular material placed in a path at 0° with respect to the direction of the electron beam striking the target is greater than the TVL, HVL, or the similar, of the material placed in a path at 180° or opposite to the electron beam direction. Hence less material is required at a larger angle (in relative to the electron beam direction) and an optimized shield design can be based on TVL value at different angles. FIGS. 7 and 9, which will be described in greater detail below, show how the TVL values change with the angle for pure tungsten and lead respectively. Therefore, as used herein, the phrase "angular function of thickness of a material in attenuating radiation to a certain level of its original value" refers to the function or dependence of Tenth-Value-Layer ("TVL"), Half-Value-Layer ("HVL"), or the similar, of a material with respect to the angular location of the material relative to the radiation source.

As used herein, the term "angle," "angular," or other grammatical equivalents refers to the deflection angle off the z-axis, which points forward along the direction of the electronic beam striking a target in producing radiation.

As used herein, the term "shield" refers to any suitable material that attenuates radiation and is configured to reduce or minimize radiation leakage from a source to protect a point of interest (POI) or to ensure that the POI has a leakage lower than the predetermined threshold. For example, the phrase "head shield" refers to a shield around a target source to confine radiation produced by the target in a particular direction and reduce radiation to a predetermined threshold in a particular direction with respect to the beam's propagation direction. The phrase "shield for a point of interest" refers to a shield configured to protect a point of interest, such as a radiation sensitive component or device in a radiation system, by shielding off radiation originated as leakage from a source or patient scatter etc. A shield can be constructed by a single piece or by a combination of two or more pieces. A shield may be configured to perform one or more functions including radiation shielding, beam collimating etc. As used herein, the phrase "leakage from a source" or "source leakage" refers to radiation leaking through a shield of the radiation source.

As used herein, the term "patient" refers to human, animal, or any artificial object (e.g. phantom) in the direct path of the radiation beam or undergoing radiation exposure.

Linac Head Shield Design

Leakage through linac system shielding components can be a significant source of unwanted radiation to the patient, other working personnel or electronic components in the radiation room. Conventionally, linac system shielding is developed based on a trial-and-error approach, which requires costly schedules, budgets and resources, and often times results in heavy and costly shielding parts and assemblies. Further, linac system leakage performance is unknown until a prototype is constructed and actual measurements are made.

In a method of constructing a head shield according to one aspect of the disclosure, the angular distribution of radiation propagating from a source and the angular function of thickness of a material in attenuating the radiation to a certain level of its original value are determined. Based on the angular distribution of radiation from the source and the angular function of thickness of the material in attenuating the radiation, the thicknesses of the material at a plurality of angular locations around the source can be calculated in order to achieve a radiation level to or less than a pre-established threshold value. A shield around the source can be then constructed based on the calculated thicknesses of the material for any angle around the radiation source.

The angular distribution of radiation intensity propagating from a source and the angular function of thickness of a material in attenuating the radiation to a certain level of its original value can be determined using Monte Carlo methods. Monte Carlo methods are known in the art and thus their detailed description is omitted herein in order to avoid obscuring description of this disclosure. In general, Monte Carlo methods are statistical simulation methods. They are a numerical solution to a problem that models objects interacting with other objects or their environment based upon simple object-object or object-environment relationships. They represent an attempt to model a system through direct simulation of the essential physics interactions of the system in question. Various aspects of Monte Carlo methods are described in A. Bielajew, "Fundamentals of the Monte Carlo Method for Neutral and Charged Particle Transport," The University of Michigan, Ann Arbor, Mich., (2001) (hereafter the "Bielajew publication"). The disclosure of the Bielajew publication is incorporated herein by reference in its entirety. The use of Monte Carlo simulation will be illustrated below in conjunction with the description of exemplary methods for designing head shields and system shields.

Although Monte Carlo can model the intended design directly, a separate simplified computing program was created, using MATLAB and a CAD program (such as Solid-Works). This reduces the total simulation time in design iteration and optimization. The thicknesses of a material needed for attenuating the radiation to or less than a threshold value can be calculated using various algorithms or computer software (hereafter "ShieldTool"). Parameters such as the angular distribution of radiation generated and propagating from a source, the angular function of thickness of a material in attenuating the radiation to a certain level of its original value, or other Monte Carlo simulation data or empirical data can be used as inputs into ShieldTool, which can then calculate the shield thickness needed for attenuating radiation to a specified value for a specified direction. The calculated 3-dimensional (3D) shielding information can be used in constructing a shield at any point around the radiation source. One exemplary ShieldTool may include a CAD program (such as SolidWorks, ProEngineering, CREO or similar) coupled to a MATLAB script and graphical user interface (GUI). SolidWorks and MATLAB are known in the art and thus their detailed description is omitted herein in order to avoid obscuring description of this disclosure. In general, the SolidWorks CAD program or an Add-on of the CAD program may generate raw data based on 3D models. Designated post-processing data analysis, such as MATLAB scripts with GUI, can be used to import the ShieldTool data and compute 3D leakage distributions around the radiation system. The ShieldTool CAD Add-on may generate a line length of the material at each angle around the source for each part of the assembly. The line lengths for all the parts are combined in post processing to calculate how much radiation attenuation will occur before any test point. Shield-Tool is generally considered a "ray tracing" program in that it looks at straight lines out from the source and generally does not incorporate secondary sources such as radiation scatter off of materials. Therefore, to incorporate the effect of e.g. patient scatter and its contribution to the dose accumulated at a particular POI, the patient scatter is modeled as a secondary point source.

Exemplary embodiments of methods for designing a head shield will now be described with reference to the figures. It should be noted that some figures are not necessarily drawn to scale. The figures are only intended to facilitate the description of specific embodiments, and are not intended as an exhaustive description or as a limitation on the scope of the disclosure.

Examples—Linac Head Shield Design

A Monte Carlo simulation was performed to provide the angular dependence of the dose lobe as a result of the physical interactions of 6 MeV electrons incident to a target button and target holder of a radiation system. The tenth-value-layers (TVLs) were also calculated for tungsten and lead. Additional TVLs for materials other than lead and tungsten can be obtained by scaling with the corresponding density. The obtained angular dependence of the dose lobe and TVLs were used to design a shield around the target. The results showed uniform leakage below a pre-established leakage threshold of 0.01% (100 ppm) for the entire angular spectrum, assuming azimuthal symmetry.

Monte Carlo Simulation Methods and Materials

Figure 2A:
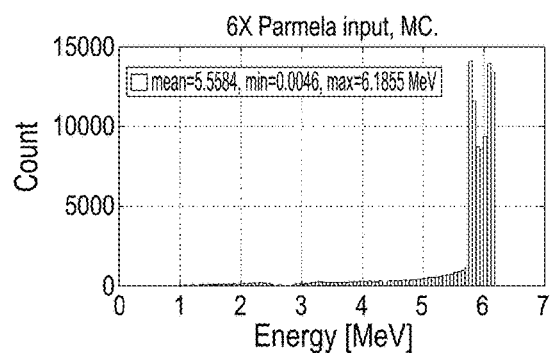
FIG. 2A schematically shows the energy spectrum of input electrons incident to the target.
Figure 2B:
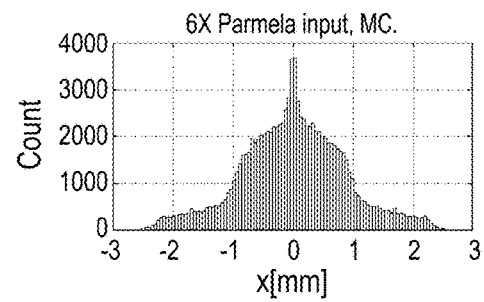
FIGS. 2B and 2C schematically show the Gaussian-like distributions of the spot x- and y-dimensions of the input electrons.
Figure 2C:
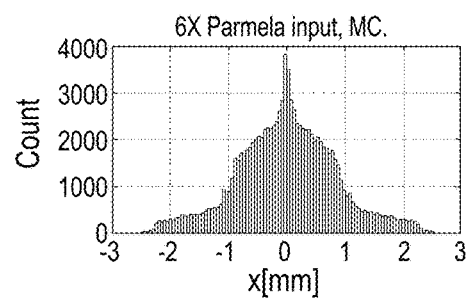

Monte Carlo simulations were conducted using Geant4 (version 9.4.p 02). The input electrons were based on an independent simulation of the electron propagation through the linear accelerator using Parmela. The electron input phase space contained ~$10^5$ particles. The energy spectrum of the input Parmela electrons is shown in FIG. 2A-2C. It is characterized by a maximum energy Emax of 6.2 MeV.

Figure 3:
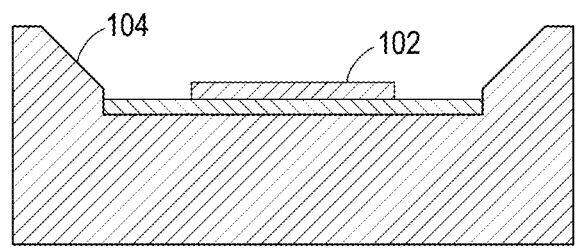
FIG. 3 schematically shows a simplified target configuration according to some embodiments of the disclosure.

FIG. 3 shows a simplified target configuration 100, comprising a target 102 and a target holder 104. In this exemplary configuration, tungsten target 102 and target holder 104 had azimuthal symmetry. The target 102 may be a transmission target.

Figure 4:
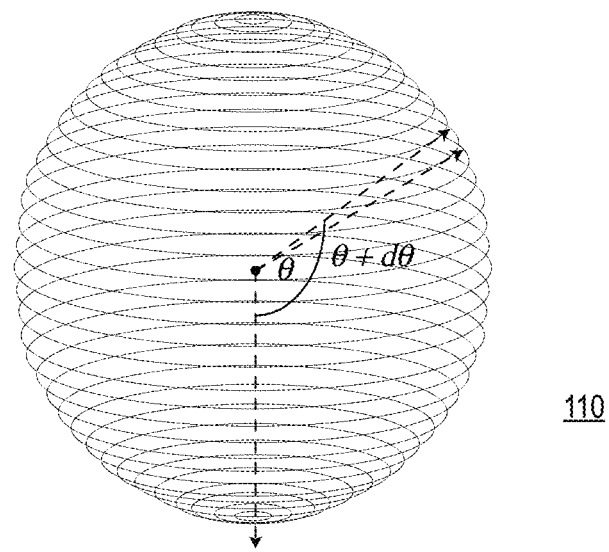
FIG. 4 schematically shows a particle fluence scorer setup for a target using a Monte Carlo simulation method according to some embodiments of the disclosure.

FIG. 4 shows a particle fluence scorer setup 110 to account for all particles reaching at a 1 m radius spherical detector using Geant4. The center of the scorer was placed on the top surface of the target button 102. Filters that allowed scoring of particles with energy in the interval $E_k \in [E_k, E_k+dE]$ and azimuthal direction in the interval $\theta_j \in [\theta_j, \theta_j+d\theta]$ were included. The energy interval [0, Emax] was divided in 100 bins, hence the energy bin size was dE=0.062 MeV. The azimuthal angle increment was set to $d\theta=0.5$ degree. Zero (0) degree points towards the patient (isocenter).

Dose Lobe and TVL Calculation

In the model described above, the particle fluence was converted to dose-to-water in order to obtain the dose lobe dependence on angle $\theta$. The particle fluence was converted to dose-to-water according to the following equation:

$$D(cGy) = \frac{1.6 \times 10^{-8}}{R^2} \Phi E \frac{\mu_{en}(E)}{\rho}, \quad [1]$$

where E is the particle energy, $\Phi$ is the particle fluence, $$\frac{\mu_{en}(E_k)}{\rho}$$

is the energy-mass absorption coefficient for water (in cm²/g), R is the distance from the origin to the detector surface (i.e. 1 m) and $1.6 \times 10^{-8}$ is a constant to convert MeV/g to cGy. This formula is valid for monoenergetic beam; for non-monoenergetic beams, it becomes Eq. [2]:

$$D(\theta_j) = \frac{1.6 \times 10^{-8}}{R^2} \sum_0^{Emax} E_k S(E_k, \theta_j) \frac{\mu_{en}(E_k)}{\rho}, \quad [2]$$

where $S(E_k, \theta_j)$ is the probability to find a particle with energy $E_k \in [E_k, E_k+dE]$ and angle $\theta_j \in [\theta_j, \theta_j+d\theta]$, and the sum is over all the detected particles with energy below Emax. To perform this conversion, the energy-mass absorption coefficient for water (i.e. tissue) was used.

To calculate the transmission factor $T(\theta_j, x)$ through a shield of thickness x, Eq. [3] was used:

$$D(\theta_j, x) = \frac{1.6 \times 10^{-8}}{R^2} \sum_0^{Emax} E_k S(E_k, \theta_j) \frac{\mu_{en}(E_k)}{\rho} B(E_k, \mu x) e^{-\mu x}, \quad [3]$$

where $B(E_k, \mu x)$ is the dose buildup factor and $e^{-\mu x}$ is the linear attenuation factor. The dose buildup factor can be expressed using the Berger equation: $B(E_k, \mu x) = 1 + C(E_k) \mu x e^{D(E_k) \mu x}$, where the dose buildup C and D coefficients for tungsten and lead were extracted from prior studies and interpolated for all energy sampling points. Buildup coefficients for various materials are disclosed in D. K. Trubey, A survey of empirical functions used to fit gamma-ray buildup factors, Oak Ridge Nat. Lab. (1966) (hereafter the "Trubey publication"). The disclosure of the Trubey publication is incorporated herein by reference in its entirety. The linear attenuation coefficient $\mu$ for tungsten and lead, respectively, was also interpolated to cover the entire set of energy sampling points. In the above equations, $\mu$ also depends on the particle energy $E_k$. The transmission factor $T(\theta_j, x)$ for a shield of thickness x corresponding to the azimuthal angle $\theta_j$ is expressed as:

$$T(\theta_j, x) = \frac{D(\theta_j, x)}{D(\theta_j, 0)}. \quad [4]$$

Simulation Results

Figure 5:
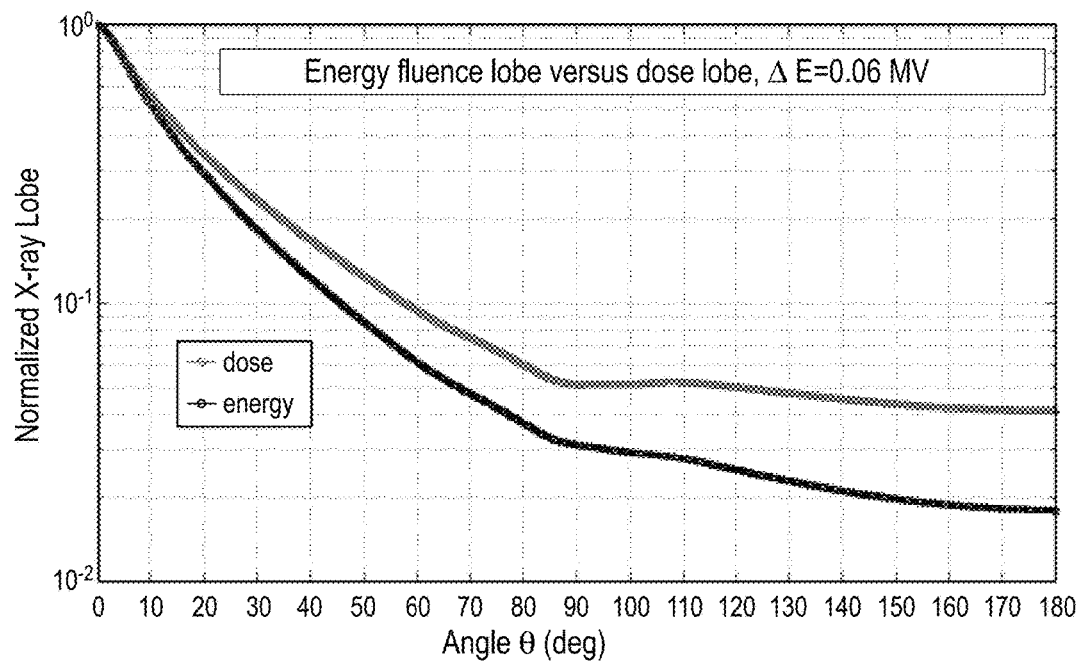
FIG. 5 shows plots of a dose lobe and an energy fluence lobe according to some embodiments of the disclosure.

FIG. 5 shows a plot of the dose lobe. The dose at each point is normalized to the central axis dose maximum. For comparison purposes, the normalized energy fluence lobe is also shown in FIG. 5. The energy fluence lobe is a summation of particle fluence weighted by the corresponding particle energy, except that the energy-mass absorption coefficient is not factored in. FIG. 5 shows that the radiation intensity is the highest on the beam's z-axis (i.e. at 0 degree). There is less intense radiation propagating in the horizontal plane (at 90 degree) and much less intense radiation is backscattered (at 180 degree). This means that different shielding amounts are needed at different angles for attenuating radiation to a uniform predetermined threshold.

Figure 6:
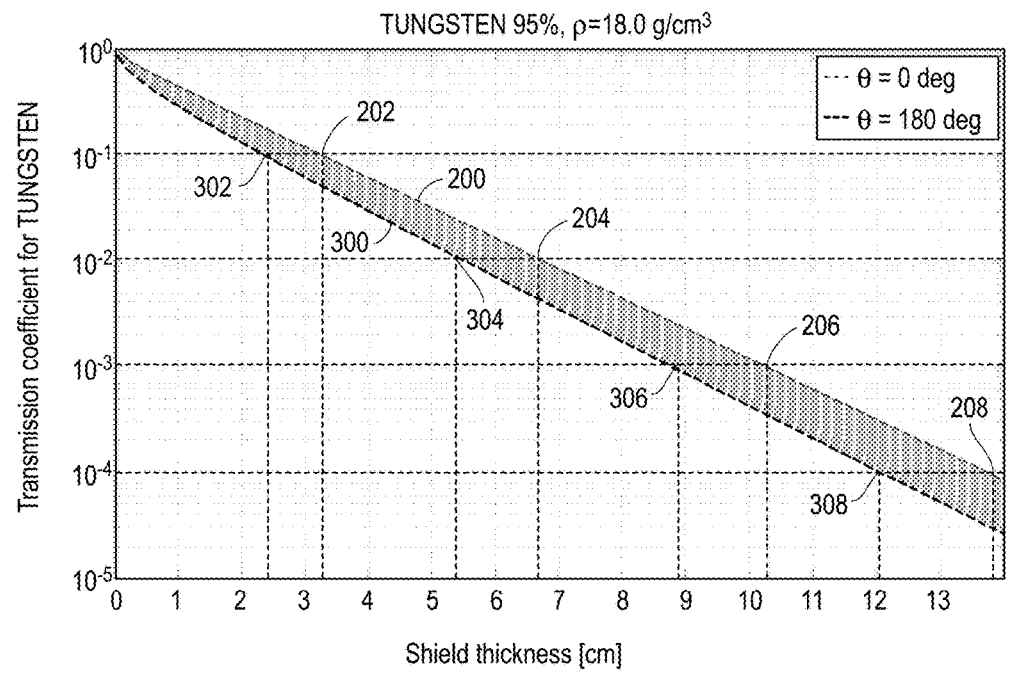
FIG. 6 shows an angular function of the transmission coefficient of tungsten according to some embodiments of the disclosure.

FIG. 6 shows the transmission coefficient of tungsten ($\rho$=18.0 g/cm3) versusshield thickness for a family of scattering angles between 0 and 180 degrees. The boundary curve 200 represents the transmission coefficient of tungsten at 0 degree (i.e. straight forward photons). The boundary curve 300 represents the transmission coefficient of tungsten at 180 degree (i.e. straight backscattered photons). The transmission coefficient of tungsten at an angle between 0 and 180 degrees can be found between the curve 200 and curve 300.

FIG. 6 shows that for tungsten the difference of $1^{st}$ TVL at 0 degree and 180 degree is 0.8 cm (3.2 cm at 0 degree (reference 202) and 2.4 cm at 180 degree (reference 302)). The difference of the $2^{nd}$ TVL at 0 and 180 degrees is 1.2 cm (6.6 cm at 0 degree (reference 204) and 5.4 cm at 180 degree (reference 304)). The difference of the $3^{rd}$ TVL at 0 and 180 degrees is 1.4 cm (10.2 cm at 0 degree (reference 206) and 8.8 cm at 180 degree (reference 306)). FIG. 6 further shows that the difference of the $4^{th}$ TVL of tungsten at 0 and 180 degrees is as much as 1.8 cm (13.8 cm at 0 degree (reference 208) and 12 cm at 180 degree (reference 308)).

FIG. 7 shows the angular dependence of individual TVLs (TVL1, TVL2, TVL3 and TVL4) and average TVL for tungsten. FIG. 7 shows that the average TVL decreases from 34.4 mm at 0 degree to 30.2 mm at 180 degree. FIG. 7 also shows that the higher the TVL order, the greater the beam hardening effect, hence the more material is needed to achieve the desired radiation attenuation. Beam hardening effect refers to the mean photon energy increase obtained as the radiation passes through more and more shield due to the stopping of the low energy photons.

Figure 8:
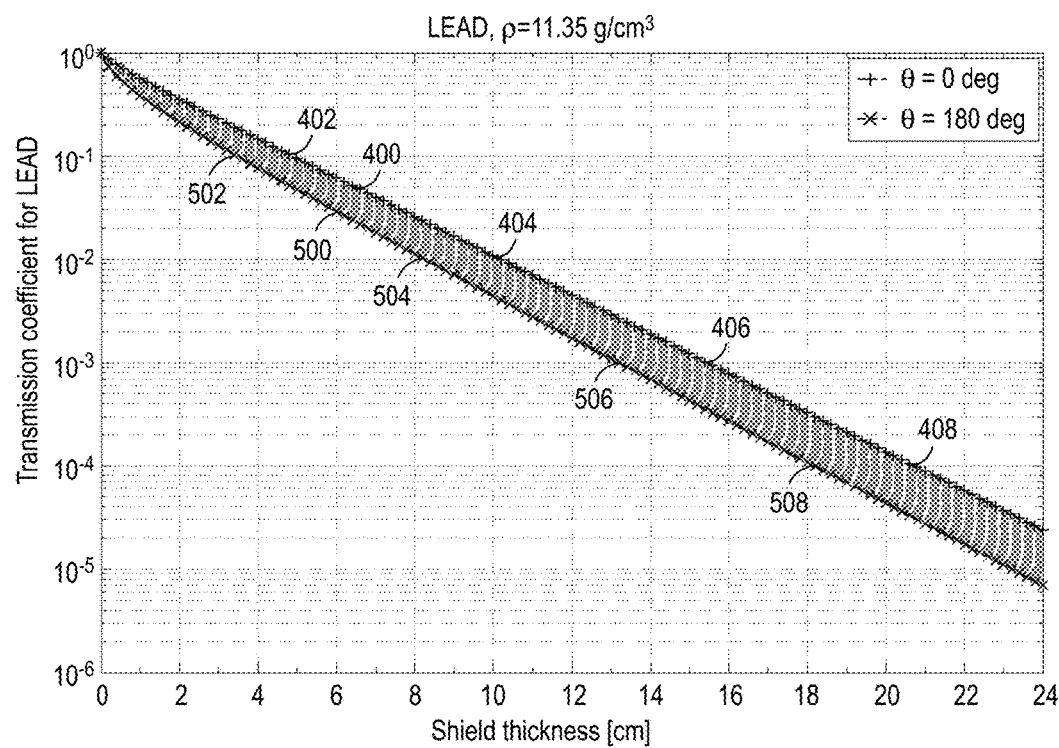
FIG. 8 shows an angular function of the transmission coefficient of lead according to some embodiments of the disclosure.

FIG. 8 shows the transmission coefficient of pure lead ($\rho$=11.35 g/cm3) versus shield thickness for a family of scattering angles between 0 and 180 degrees. The boundary curve 400 represents the transmission coefficient of lead at 0 degree. The boundary curve 500 represents the transmission coefficient of lead at 180 degree. The transmission coefficient of lead at an angle between 0 and 180 degree can be found between the curve 400 and curve 500.

FIG. 8 shows that for lead the difference of $1^{st}$ TVL at 0 degree and 180 degree is 1.5 cm (5.0 cm at 0 degree (reference 402) and 3.5 cm at 180 degree (reference 502)). The difference of the $2^{nd}$ TVL at 0 and 180 degrees is 2.0 cm (10.5 cm at 0 degree (reference 404) and 8.5 cm at 180 degree (reference 504)). The difference of the $3^{rd}$ TVL at 0 and 180 degrees is 2.1 cm (15.6 cm at 0 degree (reference 406) and 13.5 cm at 180 degree (reference 506)). FIG. 8 further shows that the difference of the $4^{th}$ TVL of lead at 0 and 180 degrees is as much as 2.5 cm (21.0 cm at 0 degree (reference 408) and 18.5 cm at 180 degree (reference 508)).

FIG. 9 shows the angle dependence of individual TVLs (TVL1, TVL2, TVL3 and TVL4) and average TVL for lead. FIG. 9 shows that the average TVL decreases from 51.8 mm at 0 degree to 45.4 mm at 180 degree. Similar to FIG. 7, the beam becomes harder as additional TVLs are inserted in the path of the beam.

Designing Head Shield

Figure 10:
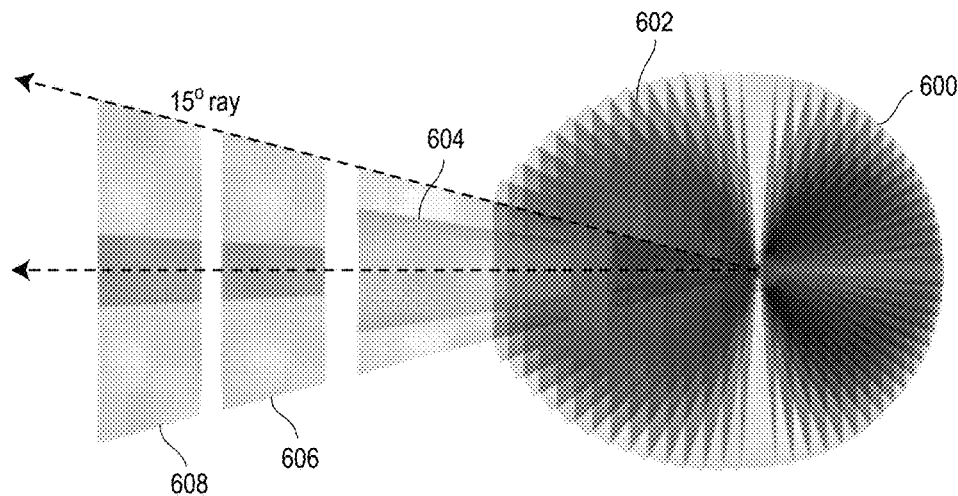
FIG. 10 shows a head shield with an Avocado-like shape around a target according to some embodiments of the disclosure.

Based on the simulated angular dose lobe and angular TVL for a specific shielding material, a shield around the target was constructed in order to lower the head leakage below a certain threshold. If the desired leakage threshold is $I_{spec}$ (normalized to an open field of 10×10 cm²), then the shield thickness at a given angle ($x(\theta_j)$) can be calculated according to the following equation:

$$x(\theta_j) = TVL(\theta_j) * [\log_{10} D(\theta_j) - \log_{10}(I_{spec})]. \quad [5]$$

where $TVL(\theta_j)$ is the average tenth-value-layer shown in FIG. 7 (for W) and FIG. 9 (for Pb). $D(\theta_j)$ is the value of the normalized dose lobe (shown in FIG. 5) corresponding to the angle $\theta_j$. By applying this procedure, an "avocado-like" shield 600 was obtained, as shown in FIG. 10. For a preliminary shield design exercise, the desired spec or leakage threshold was 100 ppm (0.01%), hence $\log_{10}(I_{spec})=-4$. An angle increment of 5° was used for $\theta_j$. The primary and secondary collimators 602, 604, as well as the proximal and distal MLCs 606, 608, were truncated such that their outer envelope followed a predetermined angle e.g. 15°. For simplicity, the primary and secondary collimators 602, 604 were drawn as cones with circular apertures having an area proximately equal to a field of 30×30 cm². Similarly, the MLC aperture, when open, had an area equal to a field of 10×10 cm². The avocado shield 602 has an inner radius of 15 mm and the outer radius is given by Eq. [5]. Avocado-like shape came from the fact that less shielding material is needed in the directions that are opposite to the incoming electron particles.

Figure 11:
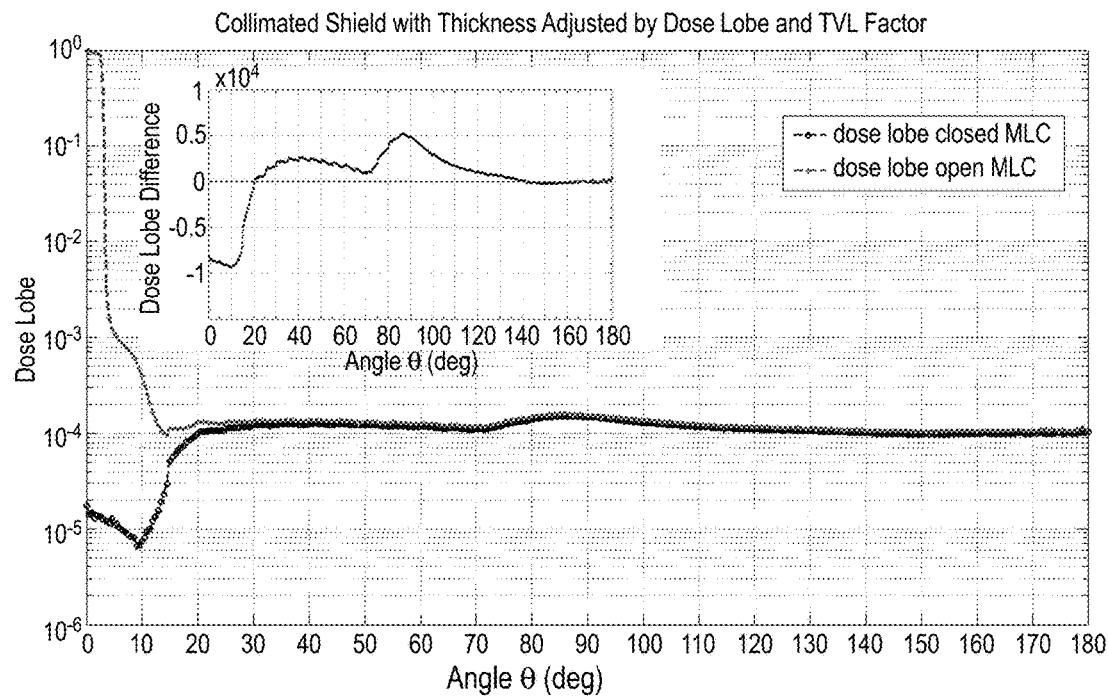
FIG. 11 shows plots of dose lobes for the shield shown in FIG. 10 according to some embodiments of the disclosure.

FIG. 11 shows plots of simulated dose lobes for the designed head shield when the MLCs 606, 608 are fully open and fully closed respectively. FIG. 11 provides information on leakage through the target shield versus angle. As described, 0.01% is a desired leakage threshold for the head shield. For angles larger than 20°, outside the in-field treatment area, the dose lobe has a substantially "flat" or uniform aspect, which is a very good output for this preliminary shield design.

Figure 12:
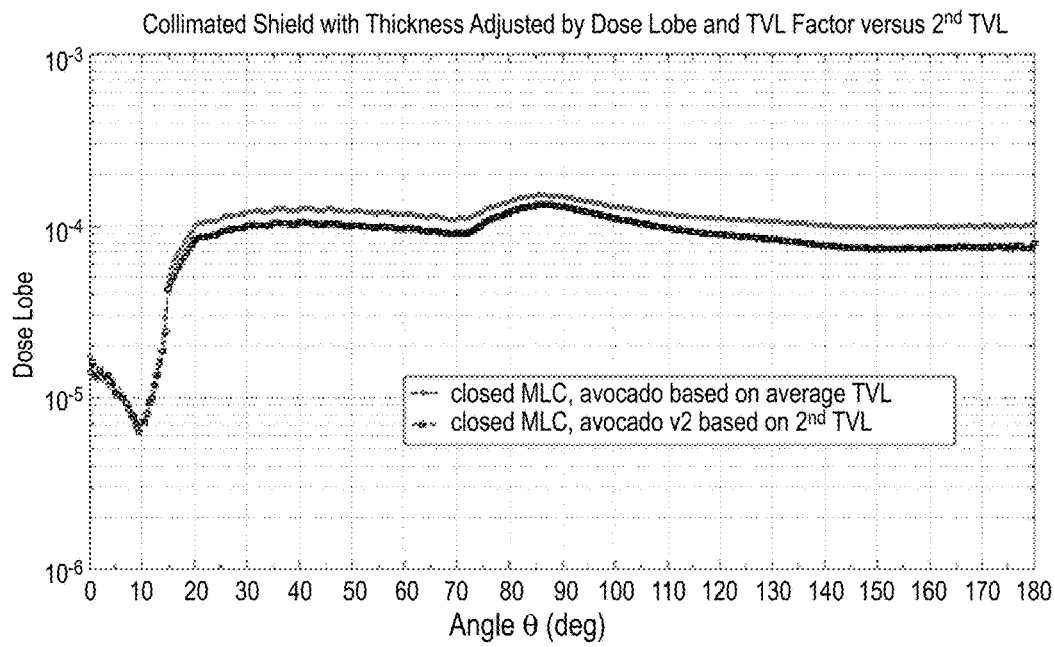
FIG. 12 shows plots of dose lobes for a collimated shield with the thickness adjusted using an iterative procedure according to some embodiments of the disclosure.

FIG. 11 further shows that the dose lobe is on average 16% larger than the desired value, with a "hump" at ~85° where the dose lobe 52% above the desired limit (see inset of FIG. 11). To correct this, a more conservative TVL can be used instead of the average TVL value. As shown in FIG. 7, the second, third and fourth TVLs are all larger than the average TVL. Since the second TVL is on average ~1.5 mm larger than the average TVL, modifying the shield thickness according to $x(\theta_j) = TVL2(\theta_j) * [4 + \log_{10} D(\theta_j)]$ would lower the dose lobe below the 0.01% specification. FIG. 12 shows that modifying the shield thickness using the second TVL can provide a uniform dose lobe with an average leakage of 94 ppm for angles between 20° and 180°, with the maximum value of 133 ppm at 85°. However, FIG. 12 also shows that building the head shield based on the $2^{nd}$ TVL angular dependence did not eliminate the "hump" and the resulting shield was too conservative beyond ~110° due to leakage being lower than the desired threshold of 100 ppm.

Optimizing Head Shield Design

In an alternative embodiment, the head shield was modified or adjusted according to the following equation:

$$\tilde{x}(\theta_j) = \widetilde{TVL}(\theta_j) * [\log_{10} D(\theta_j) - \log_{10}(I_{spec})], \quad [6]$$

where $\widetilde{TVL}(\theta_j)$ represents a modified or corrected angular TVL curve:

$$\widetilde{TVL}(\theta_j) = \frac{x(\theta_j)}{\log_{10} D(\theta_j) - \log_{10} D^{coll}(\theta_j)}. \quad [7]$$

Figure 13:
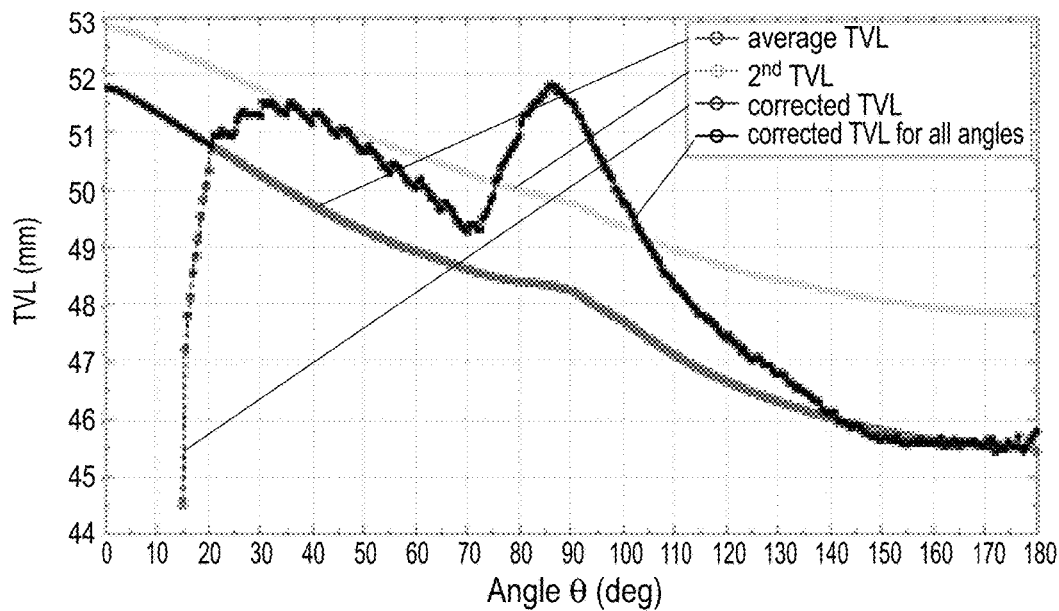
FIG. 13 shows a modified TVL for lead over an angular range according to some embodiments of the disclosure; curves of the average TVL and $2^{nd}$ TVL are shown; a corrected TVL angular dependence is derived to compensate for the over- and under-designed shield.

In Eq. (7), $x(\theta_j)$ is given by Eq. [5] and $Dc^{coll}(\theta_j)$ is the dose lobe shown in FIG. 12. The modified or corrected angular TVL is shown in FIG. 13 (blue squares), along with the average TVL and $2^{nd}$ TVL for lead. Note that the modified TVL shows a "hump" at 85° which was expected to eliminate the leakage hump previously seen in FIGS. 11 and 12 where the TVL values used were not large enough to reduce the leakage below the desired specification of 100 ppm. At angles smaller than 20° the average TVL values were used since, as shown in FIG. 11, they ensured a leakage well below 100 ppm. The modified TVL curve for all angles is shown by the black dot curve.

This modification recipe can be applied iteratively to improve the TVL curve. For example, in a case where the leakage specification changed from 100 ppm to 400 ppm, a new head shield was constructed and the modification recipe was applied one more time according to the following equation:

$$TVL''(\theta_j) = \frac{\widetilde{TVL}(\theta_j) * [\log_{10} D(\theta_j - \log_{10} I''_{spec})]}{\log_{10} D(\theta_j) - \log_{10} D^{coll}(\theta_j)} \quad [8]$$

Figure 14:
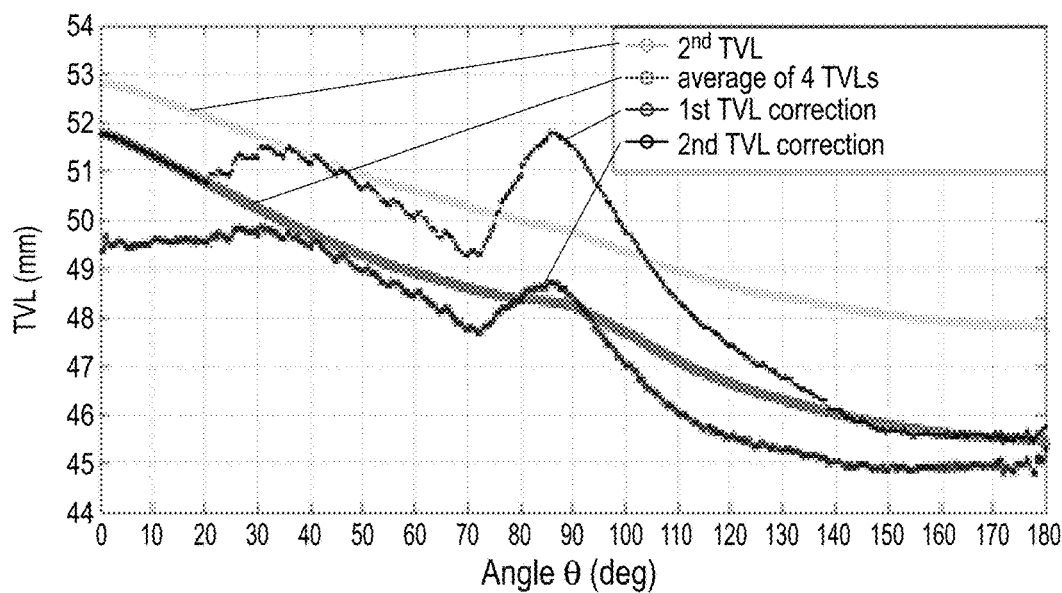
FIG. 14 shows an optimized angular dependence for the TVL for lead for an alternative head shield designed to achieve a more relaxed leakage threshold (400 ppm) according to some alternative embodiments of the disclosure.

The second modification led to the results shown in FIG. 14 by the curve of $2^{nd}$ TVL correction. The TVL curve is less conservative than the previous dependence since the leakage requirement was relaxed from 100 to 400 ppm. This TVL correction recipe can be applied to any radiation source shield, leading to a cost-efficient, optimal solution while ensuring that the shield weight is only driven by the desired predetermined leakage threshold.

Linac System Shield Design

In a radiation system, there are electronic components or devices that are vulnerable to radiation exposure. Components or devices that are radiation sensitive include power supplies, various device controllers, computers, display panels, cameras, sensors, and various electronic components on printed circuit boards. The radiation sensitive components or devices may be located in a gantry or rotatable with the radiation source. The radiation sensitive components or devices may also be located in a stand, patient support (e.g. couch or other lifting platforms), or other structures which do not rotate with the radiation source when in operation. Local shielding for the radiation sensitive components or devices may be needed to ensure their normal functions or prolong their useful life span. In this disclosure, the phrase "point of interest" or "POI" may be used to refer to a component or device in a radiation system that is sensitive to radiation exposure and requires a shield to block or minimize radiation deposited on it.

Radiation deposited on a POI may come from radiation leakage of the linac system and the patient scatter as a result of the primary beam hitting the patients. Patient scatter may be significant to some POIs and less to the others depending on if the POI rotates with the source, the distance and the angel to the source. The shielding design according to this disclosure considers patient scatter in addition to the leakage from the primary source.

The distribution of radiation propagating from a primary radiation source or secondary source placed at the machine isocenter (also coincidental with the patient's tumor) is a function of the corresponding spatial angles. More radiation propagates in a forward direction and less radiation propagates in a horizontal plane relative to the source and much less radiation backscatters. As such, a radiation sensitive component or device may receive same or different amounts of radiation, depending on the location of the component or device in the radiation system. By way of example, a power supply fixedly located in a radiation system may receive different amounts of radiation from source leakage and patient scatter during operation of the system since both the distance and the angle between the power supply and the radiation source may change as the radiation source rotates around the patient. On the other hand, an electronic controller located in a gantry or rotatable with a radiation source receives the same amount of radiation during operation of the system because both the distance and the angle between the electronic controller and the radiation source and/or isocenter remain unchanged as the radiation source rotates assuming the patient is somewhat cylindrical-like, centered at iso-center of the system. Therefore, the "rotational factor," whether or not a radiation sensitive component or device rotates with the primary source during operation, needs be considered in designing a local shield for the component or device.

In modern radiation therapy, treatments are often delivered using intensity modulated radiotherapy (IMRT), which involves shaping treatment fields with multileaf collimators (MLCs). In IMRT, both the shape of the treatment field and radiation fluence may be changed or "modulated" such that the radiation fluence to healthy organs or tissue is as low as possible to avoid risks such as secondary malignancies. This means that the "modulation factor," i.e., radiation fluence blocked by MLCs during IMRT, need be accounted for in the calculation of patient scatter contribution to the net accumulated radiation deposited for the component to be shielded. In general higher modulation factor indicates a higher radiation generated from the linac system, hence higher radiation leakage to POIs from the primary source. Therefore, modulation factor needs to be considered in shielding design. Patient scatter contribution to radiation deposited on a component is typically obtained by directing an open or unmodulated treatment field of a specific size to a given phantom.

Therefore, in a method of designing a radiation shield for a point of interest in a radiation system, both the target source and scatter source are included in the ShieldTool framework to improve the overall shielding calculation. With the target lobe centered at the target and the patient scatter lobe centered at isocenter, radiation level at all points of interest can be calculated from the two sources respectively and the total radiation at certain point can be obtained by summing up the results. In addition, both the rotational factor and modulation factor (MF) may be accounted for in the shielding design.

In one embodiment, a method of constructing a radiation shield for a point of interest (POI) at a location in a radiation system is provided. The radiation system comprises a movable source configured to generate radiation to be delivered to an isocenter in a patient. The POI is movable with the source. According to this embodiment, the radiation reaching at the location of the POI through source leakage and the radiation reaching at the location of the POI from patient scatter are determined respectively. The accumulated radiation at the location of the POI is calculated by summing the contributions. A shield for the POI is constructed based on the accumulated radiation at the location of the POI.

In a further embodiment, a method of constructing a radiation shield for a point of interest (POI) at a location in a radiation system is provided. The radiation system comprises a movable source configured to generate radiation to be delivered to an isocenter in a patient. The POI is non-movable with the source. According to this embodiment, a plurality of locations of the source with respect to the location of the POI are selected to account for the 360 degree rotation of the radiation source around the isocenter. At each of the plurality of locations of the source, a first portion of radiation reaching at the location of the POI through source leakage, and a second portion of radiation reaching at the location of the POI through patient scatter are determined respectively. An average first portion of radiation and an average second portion of radiation are calculated. The accumulated radiation reaching at the location of the POI is calculated by summing the average first portion and the average second portion of radiation. A shield for the POI is constructed based on the accumulated radiation at the location of the POI. More locations (angels) from the fixed POIs to the rotating source can be added and averaged throughout 360 degree rotation, based on dynamic treatments which utilize many different gantry angles in relative to tumors.

Exemplary methods of designing local shields for radiation sensitive components will now be described with reference to the figures. It should be noted that the specific examples and figures are only intended to facilitate the description of embodiments, and are not intended as an exhaustive description or as a limitation on the scope of the disclosure.

Figure 15:
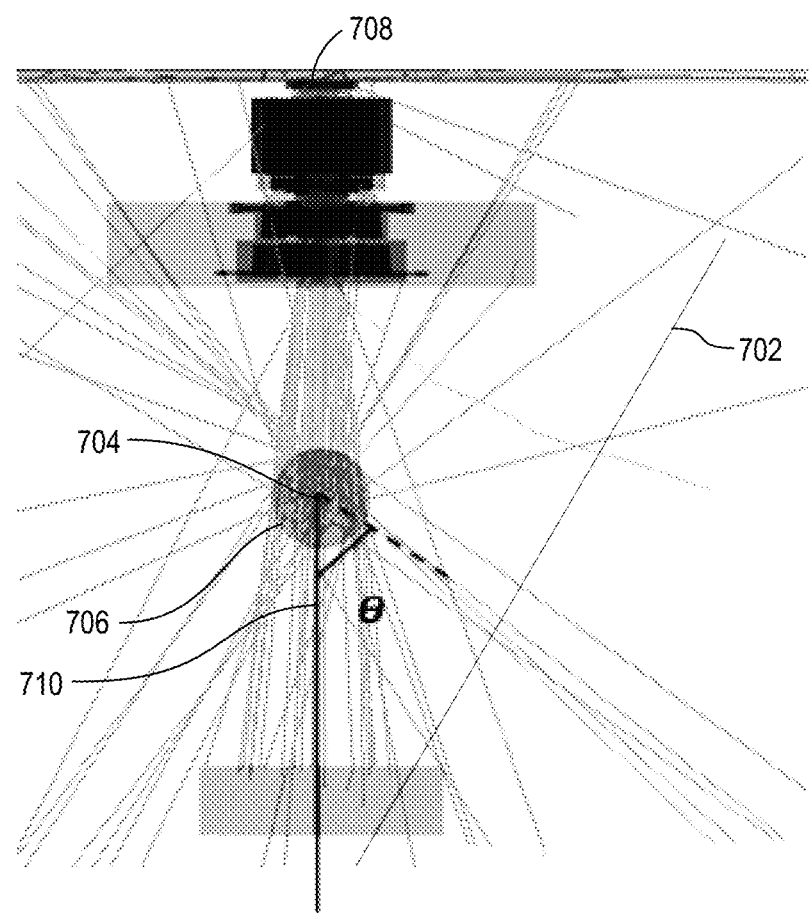
FIG. 15 schematically shows a scorer setup for patient scatter calculation using a Monte Carlo simulation method according to some embodiments of the disclosure.

Examples—Linac System Shield Design
Monte Carlo Simulation Methods and Materials Monte Carlo simulations with an estimated treatment field size were performed in order to create a model for patient scatter. FIG. 15 shows an exemplary model layout for patient scatter simulations. A scoring plane 702 of 2×2 m² at 500 mm from the isocenter 704 was rotated around the y-axis along the length of the patient 706. The patient 706 was modeled as a water cylinder, with a height of 165 cm and a diameter of 22.6 cm. These dimensions are representative for small patients since the scatter is more reduced for larger patients. The center of the cylinder was placed in the radiation machine isocenter 704 at 1000 mm from the target 708. The cylindrical symmetry of the water phantom 706 allowed a rotation of the planar scorer 702 around the phantom center 704, equivalent to rotating the source 708 around the patient 706 and keeping the scorer 702 fixed. The angle θ measured with respect to the beam's axis 710 is shown in FIG. 15. Although the patient scatter contribution depends on the size of the patient 706, previous simulations revealed that leakage in large patients is smaller than that in small patients (i.e. radiation attenuation is the dominant effect compared to patient scatter). Hence, a small patient was chosen in this example in order to avoid an over-optimistic model.

Phase space files were recorded at 500 mm from the isocenter 704 and the angle θ was incremented from 15, 30, 45, 60, 90, 120 and 150 degrees. Angles below 15 degrees were not considered because they project inside the primary radiation beam. The data files were binned using a 10×10 mm² bin size to calculate photon energy fluence. The energy fluence profiles were normalized to the on-axis output at 1000 mm from source for an open field of 10×10 cm² with no patient in the beam line. The result of this calculation is also referred to as relative leakage.

The input electrons were based on the particle-in-cell codes phase space with ~10⁵ particles, with an energy spectrum shown in FIGS. 2A-2C. Monte Carlo simulations with Geant4 (version 9.4.p 02) were launched on Amazon EC2 computing cloud using the c1.x large cluster. For the MLCs, template was used to simulate an open 18 cm square field.

Figure 16:
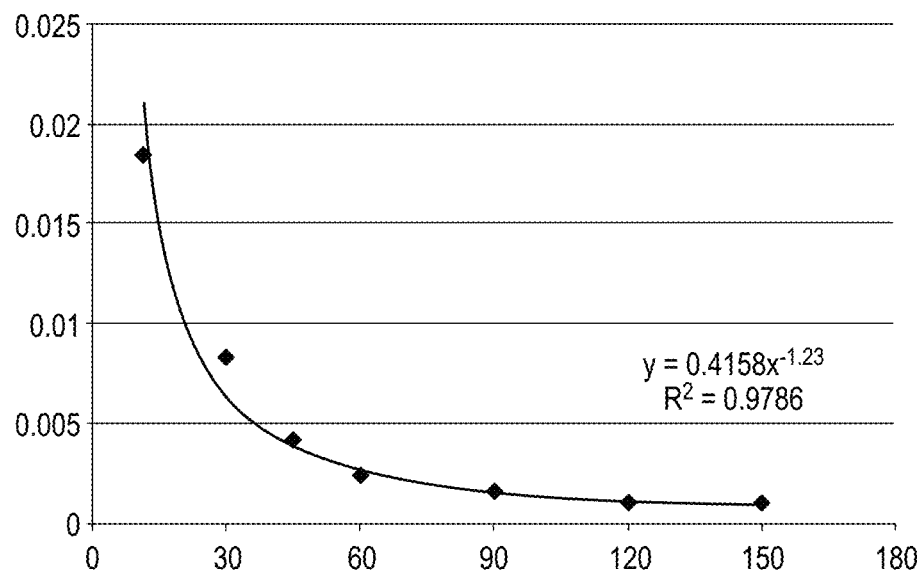
FIG. 16 shows a plot of patient scatter lobe versus angle with respect to the forward beam direction, measured from the center of the patient, according to some embodiments of the disclosure.

FIG. 16 is a plot of a patient scatter lobe, showing the relative intensity (vertical axis) versus scattering angles (horizontal axis). The dose at each point is normalized to the central axis dose output. FIG. 16 shows that more patient scatter occurs in the path of primary beam (at 0 degree). There is less patient scattering in the horizontal plane (at 90 degree) and even less patient scatter contributions at angles larger than 90 degrees.

Figure 17:
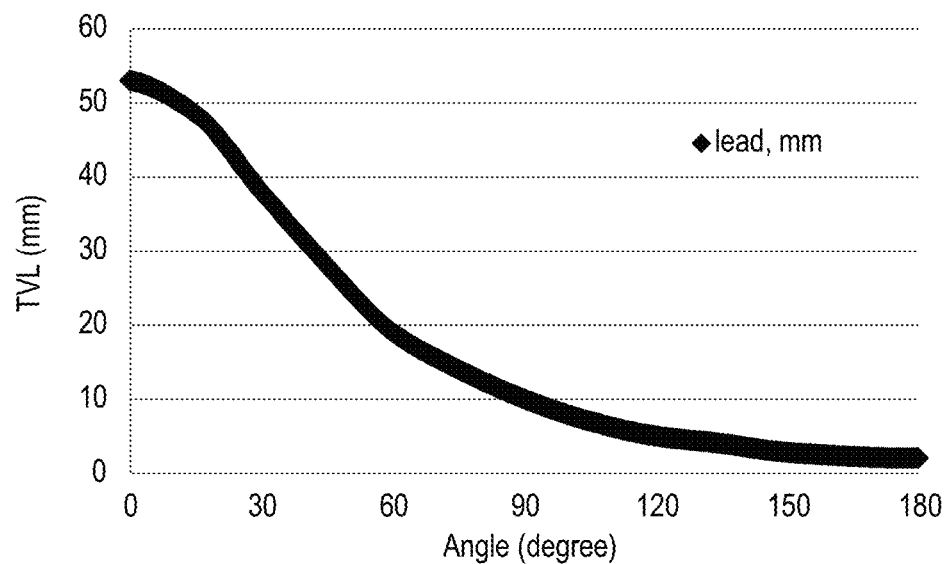
FIG. 17 shows an angular dependence of patient scatter TVL according to some embodiments of the disclosure.

FIG. 17 is a plot showing the angular dependence of the patient scatter TVL (vertical axis) versus scattering angles (horizontal axis) for lead. FIG. 17 shows that the TVL of lead decreases from 52 mm at 0 degree of scattering angle to approximately 10 mm at 90 degree of scattering angle and approximately 1 mm at 180 degree of scattering angle.

Shielding Design for Rotational Components

Figure 18:
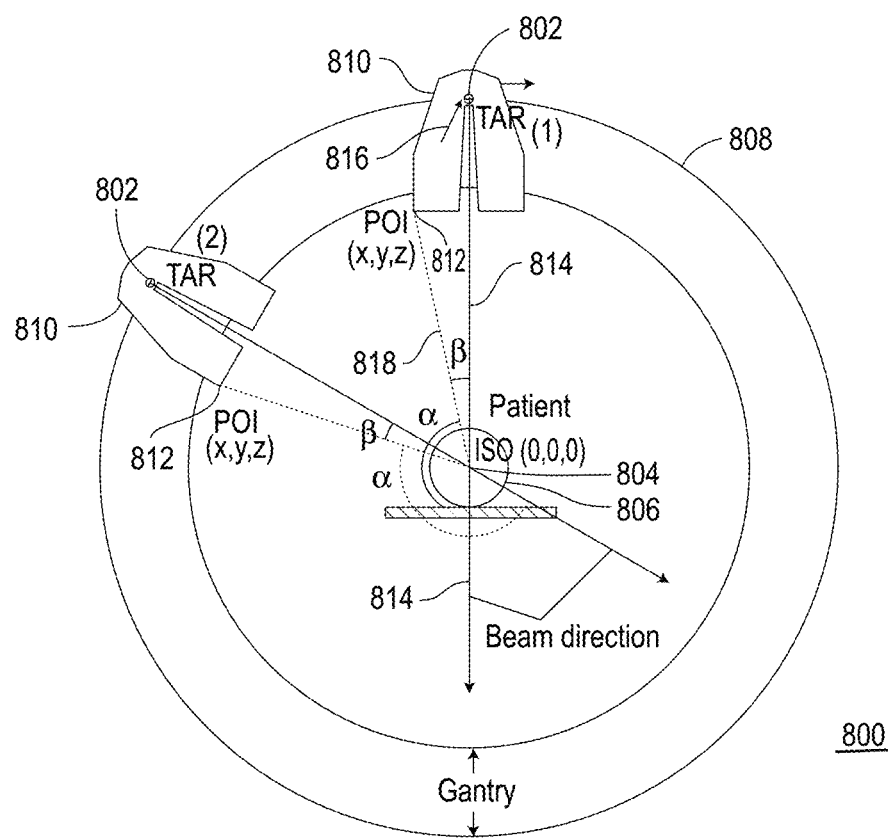
FIG. 18 schematically shows a radiation system performing a gantry rotation, illustrating a method of designing a shield for a rotational component according to some embodiments of the disclosure.

FIG. 18 schematically shows a radiation system 800 illustrating an exemplary method for designing a radiation shield for a rotational component according to some embodiments of the disclosure. As shown, the radiation system 800 includes a movable source 802 configured to generate radiation to be delivered to an isocenter 804 in a patient 806. By way of example, the radiation source 802 may be supported by a gantry 808 which may rotate around the patient 806 in a circular orbit. The head shield 810 around the source 802 is configured to collimate the radiation beam to the desired treatment field at isocenter and minimize radiation leakage in the other directions. A point of interest 812 e.g. an MLC controller or other radiation sensitive component may be rotatable with the source 802.

To facilitate description, the location of the POI is referenced at (x, y, z) in a coordinate system with the target source 802 as the reference origin (0, 0, 0). In an alternative coordinate system with the isocenter 804 in the patient 806 as the reference origin (0, 0, 0), the location of the POI 812 can be referenced at (x', y', z'). There is a 1 m shift between the target source reference origin and the isocenter reference origin. The spatial angle (θ) of the POI 812 with respect to the target source 802 is measured from the beam direction 814 to a direction 816 from the target 802 to the POI 812. The patient scatter angle (α) is measured from the beam direction 814 to a direction 818 from the isocenter 804 to the POI 812.

Still referring to FIG. 18, as the source 802 rotates around the patient 806 from location (1) to location (2), the spatial angle (θ) of the POI 812 with respect to the target source 802 remains unchanged. The patient scatter angle (α) also remains unchanged. Furthermore, the distance from the target source 802 to the POI 812 and the distance from the isocenter 804 to the POI 812 maintain constant. This configuration can be referred to as a "static mode." The accumulated leakage L (x, y, z) received by the POI 812 can be determined by summing the leakage from the target source (L_TAR) and patient scatter (L_PS) contributions.

$$L(x,y,z) = L\_TAR(d,\theta) + L\_PS(d',\alpha)/MF \qquad [9]$$

where (x, y, z) are the coordinates of the POI 812 with respect to the target reference system $[d=(x^2+y^2+z^2)^{0.5}]$, (x',y',z') are the coordinates of the POI 812 with respect to the patient scatter reference system $[d'=(x'^2+y'^2+z'^2)^{0.5}]$, angle (θ) is the spatial angle of the POI 812 with respect to the target source 802, angle (α) is the patient scatter angle, and MF is the modulation factor, a correction factor applied to the patient scatter contribution (L_PS) to account for the average MU "wasted" per cGy delivered to the tumor. The modulation factor can be empirically determined.

Modulation factor can be estimated from the total dose generated by the linac system divided by the delivered dose to the iso-center. Alternative method is to sum up patient scatter and primary source leakage (Eq. [9]) using an averaged modulated field size in the calculations (as well as the measurements). Here, MF=1, when an averaged modulated field size is used. The averaged modulated field size can be calculated by field size area divided by the modulation factor. For example, an averaged field size of 16 cm×16 cm with modulation factor of 4 from the dynamic treatment plan can be translated to averaged modulated field size of 8 cm×8 cm, in which modulation factor 1 is used in Eq. [9]. The target contribution and the patient scatter contribution of Eq. [9] are resulted from the field size of 8 cm×8 cm in this case.

The target source leakage contribution to the accumulated leakage at the POI 812 can be determined according to the following equation:

$$L\_TAR(d,\theta) = L_{TAR}(\theta)/d^2, \text{ where } d=(x^2+y^2+z^2)^{0.5} \qquad [10]$$

Eq. [10] shows that the target source leakage contribution depends on the spatial angle (θ) of the POI 812 with respect to the target 802 and the distance from the POI 812 to the target 802. Target leakage contribution decreases as the distance to the POI squared. The spatial angle (θ) appears in the multiplication factor $L_{TAR}(\theta)$ which can be determined by Monte Carlo simulation and is given by the target dose lobe, as illustrated in FIGS. 5-9.

The patient scatter contribution to the accumulated dose at the POI 812 can be determined according to the following equation:

$$L\_PS(d',\alpha) = L_{PS}(\alpha)/d'^2, \text{ where } d'=(x'^2+y'^2+z'^2)^{0.5} \qquad [11]$$

Eq. [11] shows that the patient scatter contribution depends on the patient scatter angle (α) and the distance of the POI 812 to the isocenter 804. The patient scatter contribution decreases as the distance squared. The patient scatter angle (α) appears in the multiplication factor $L_{PS}(\alpha)$ which can be determined by Monte Carlo simulation and is given by the patient scatter lobe, as illustrated in FIG. 16.

A local shield around the POI 812 can be constructed according to the accumulated dose deposited at the POI 812 and the angular dependence of the TVLs of the material constructing the shield.

Shielding Design for Non-Rotational Components

FIG. 19 schematically shows a radiation system 900 illustrating an exemplary method of designing a shield for a non-rotational component according to some embodiments of the disclosure. As shown, the radiation system 900 includes a movable source 902 configured to generate radiation to be delivered to an isocenter 904 in a patient 906. By way of example, the radiation source 902 may be supported by a gantry 908 which may rotate around the patient 906 in a circular orbit. The head shield 910 around the source 902 is configured to collimate the radiation beam to the desired treatment field at isocenter and minimize radiation leakage in the other directions. A point of interest 912 e.g. a power supply or other radiation sensitive component may be fixedly located in the system 900 or do not rotate with the source 902.

The location of the POI 912 can be referenced at (x, y, z) in a coordinate system with the target source as the reference origin (0, 0, 0). In an alternative coordinate system with the isocenter 904 in the patient 906 as the reference origin (0, 0, 0), the location of the POI 912 can be referenced at (x', y', z'). The spatial angle (θ) of the POI 912 with respect to the target source 902 is measured from the beam direction 914 to a direction from the target 902 to the POI 912. The patient scatter angle (α) is measured from the beam direction 914 to a direction from the isocenter 904 to the POI 912.

Figure 19A:
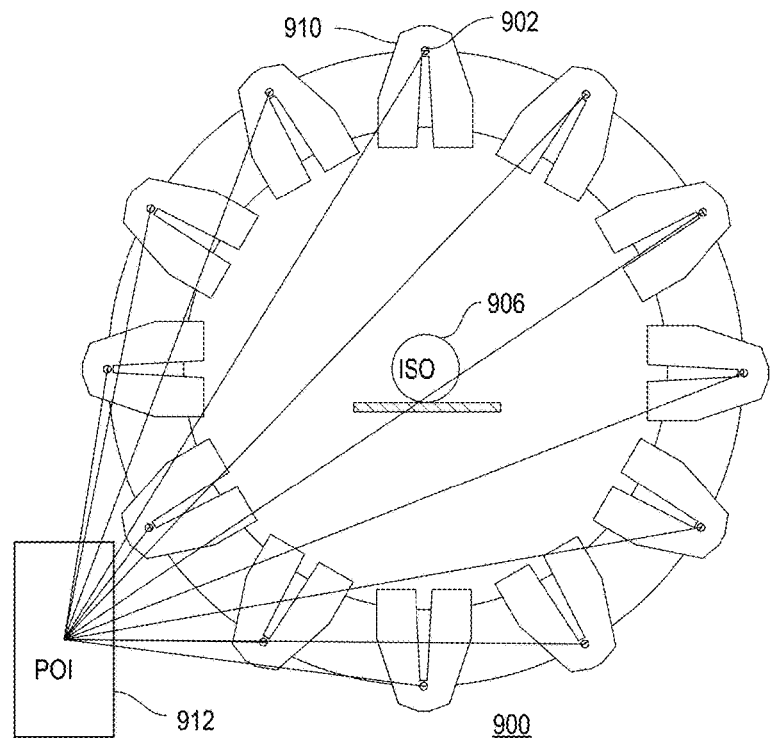
FIGS. 19A and 19B schematically show a radiation system illustrating a method of designing a shield for a non-rotational component according to some embodiments of the disclosure.
Figure 19B:
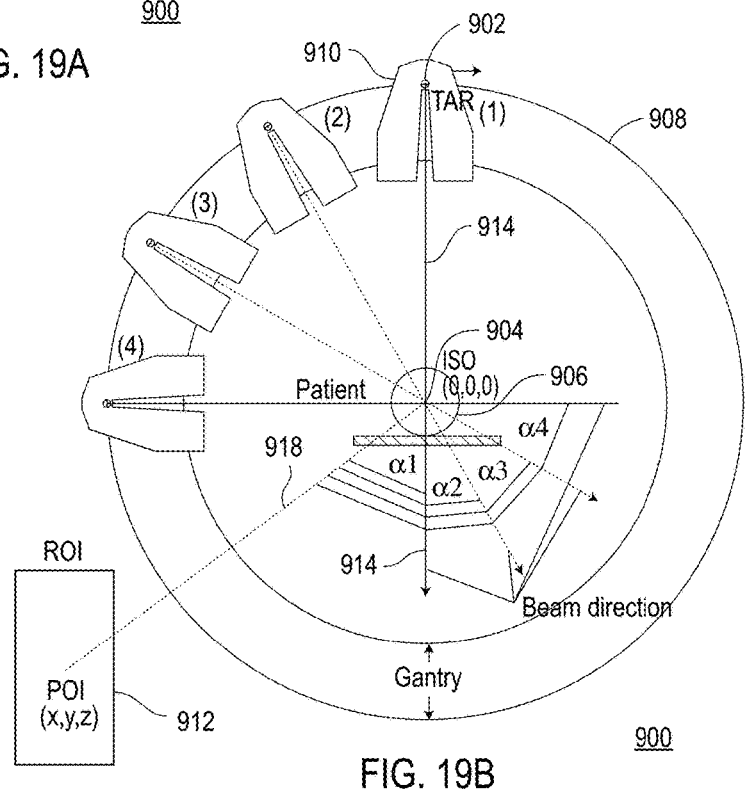

Still referring to FIGS. 19A-19B, as the source 902 rotates during operation e.g. from location (1) to location (2), (3), or (4), both the spatial angle (θ) of the POI 912 with respect to the target source 902 and the distances from the target source 902 to the POI 912 change. Further, as the source 902 rotates from location (1) to location (2), (3), or (4), the patient scatter angles ($\alpha_i$), as measured from the beam direction 914 to a direction 918 from the isocenter 904 to the POI 912, also changes from $\alpha_1$ to $\alpha_2$, $\alpha_3$, or $\alpha_4$. This configuration can be referred to as a "360 degree mode" since the gantry can fully rotate around the isocenter. This also implies that a sampling procedure should be implemented to account for the spatial variations at POI as the radiation source orbits around the isocenter.

To account for these variations, the target source leakage ($L\_TAR_i$) and patient scatter ($L\_PS_i$) contributions can be averaged over incremental angles $\alpha_i$:

$$L(x,y,z) = \Sigma_{\alpha i=0}^{360°} L_{TAR}^i + L_{PS}^i \qquad [12]$$

where (x, y, z) are the Cartesian coordinates of the POI 912 in the target coordinate reference system.

The target source leakage contribution at a particular spatial angle ($L\_TAR_i$) and patient scatter contributions at a particular scatter angle ($L\_PS_i$) can be determined using the equations described above in conjunction with the calculation for rotational components.

Those skilled in the art will appreciate that various other modifications may be made within the spirit and scope of the invention. All these or other variations and modifications are contemplated by the inventors and within the scope of the invention.

What is claimed is:

1. A method of designing a radiation shield for a point of interest (POI) at a location in a radiation system, where the POI is a component of the radiation system that is sensitive to radiation, the radiation system comprising a movable source configured to generate radiation to be delivered to an isocenter in a patient, the POI being movable with the source, the method comprising:
   determining a first portion of radiation intensity reaching the location of the POI originated from the source;
   determining a second portion of radiation reaching the location of the POI due to patient scatter originated from the isocenter;
   calculating accumulated radiation at the location of the POI by at least summing the first and the second portions of radiation; and
   constructing a shield for the POI based on the accumulated radiation at the location of the POI.

2. The method of claim 1 wherein the source is rotatable about the isocenter and the POI is rotatable with the source.

3. The method of claim 2 wherein the step of determining the first portion of radiation reaching at the POI comprises determining an angular distribution of radiation propagating from the source.

4. The method of claim 3 wherein the angular distribution of radiation from the source comprises an angular distribution of radiation dose.

5. The method of claim 3 wherein the angular distribution of radiation from the source is determined using a Monte Carlo method.

6. The method of claim 3 wherein the first portion of the radiation reaching at the location of the POI is determined according to the following equation:

$$L_{TAR}(\theta)/d^2$$

where d represents a distance from the POI to the source, θ represents a spatial angle of the POI with respect to the source, and $L_{TAR}(\theta)$ represents a value of the angular distribution of radiation from the source.

7. The method of claim 1 wherein the determining of the second portion of radiation reaching at the location of the POI comprises determining an angular distribution of radiation of patient scatter propagating from the isocenter.

8. The method of claim 7 wherein the angular distribution of radiation of patient scatter comprises an angular distribution of radiation dose.

9. The method of claim 7 wherein the angular distribution of radiation of patient scatter is determined using a Monte Carlo method.

10. The method of claim 7 wherein the second portion of radiation is determined according to the following equation:

$$L_{PS(\alpha)}/d'^2$$

where d' represents a distance from the POI to the isocenter, α represents a spatial angle of the POI with respect to the isocenter, and $L_{PS}(\alpha)$ represents a value of the angular distribution of radiation of patient scatter when irradiated with an unblocked beam.

11. The method of claim 10 further comprising determining a modulation factor (MF) of the unblocked beam, and determining the second portion of radiation according to the following equation:

$$L_{PS}(\alpha)/d'^2/MF.$$

12. The method of claim 11 wherein the modulation factor is determined by dividing a total dose generated by the radiation system with a delivered dose to the isocenter.

13. The method of claim 1 wherein the accumulated radiation is determined according to the following equation using an averaged modulated field size:

$$L(x, y, z) = L\_TAR(d, \theta) + L\_PS(d', \alpha)$$

wherein L (x, y, z) represents the accumulated leakage, $L\_TAR(d, \theta)$ represents the first portion of radiation, $L\_PS(d', \alpha)$ represents the second portion of radiation, d represents a distance from the POI to the source, θ represents a spatial angle of the POI with respect to the source, d' represents a distance from the POI to the isocenter, α represents a spatial angle of the POI with respect to the isocenter; and
   wherein the averaged modulated field size is determined by a field size area divided by a modulation factor.

14. A method of constructing a radiation shield for a point of interest (POI) at a location in a radiation system, where the POI is a component of the radiation system that is sensitive to radiation, the radiation system comprising a movable source configured to generate radiation to be delivered to an isocenter in a patient, the POI being non-movable with the source, the method comprising:

selecting a plurality of locations of the source with respect to the location of the POI, and at each of the plurality of locations of the source:

determining a first portion of radiation reaching the location of the POI originated from the source;

determining a second portion of radiation reaching the location of the POI due to patient scatter originated from the isocenter;

calculating an average first portion of radiation;

calculating an average second portion of radiation;

calculating accumulated radiation reaching at the location of the POI by at least summing the average first portion and the average second portion of radiation;

constructing a shield for the POI based on the accumulated radiation at the location of the POI.

15. The method of claim 14 wherein the source is rotatable about the isocenter in the patient and the POI is stationary relative to the isocenter.

16. The method of claim 15 wherein the plurality of locations of the source are spaced apart in substantially equal angular increments along a circular orbit.

17. The method of claim 16 wherein the plurality of locations of the source include 12 locations substantially equally spaced apart in 30 degrees in a circular orbit.

18. The method of claim 16 wherein the step of determining the first portion of radiation at the POI comprises determining an angular distribution of radiation propagating from the source.

19. The method of claim 18 wherein the angular distribution of radiation from the source comprises an angular distribution of radiation dose.

20. The method of claim 18 wherein the angular distribution of radiation from the source is determined using a Monte Carlo method.

21. The method of claim 18 wherein the first portion of the radiation is determined according to the following equation:

$$L_{TAR}(\theta)/d^2$$

where d represents a distance from the POI to the source at one of the plurality of locations, θ represents a spatial angle of the POI with respect to the source at the one of the plurality of locations, and $L_{TAR}(\theta)$ represents a value of the angular distribution of radiation from the source at the one of the plurality of locations.

22. The method of claim 14 wherein the determining of the second portion of radiation comprises determining an angular distribution of radiation scattered from the isocenter.

23. The method of claim 22 wherein the angular distribution of radiation from the isocenter comprises an angular distribution of radiation dose.

24. The method of claim 22 wherein the angular distribution of radiation from the isocenter is determined using a Monte Carlo method.

25. The method of claim 22 wherein the second portion of radiation is determined according to the following equation:

$$L_{PS(\alpha)/d'^2}$$

where d' represents a distance from the POI to the isocenter, α represents a spatial angle of the POI with respect to the isocenter when the source is at one of the plurality of location, and $L_{PS}(\alpha)$ represents a value of the angular distribution of radiation from the isocenter when irradiated with an unblocked beam from the source at the one of the plurality of locations.

26. The method of claim 25 further comprising determining a modulation factor (MF) of the unblocked beam, and determining the second portion of radiation according to the following equation:

$$L_{PS}(\alpha)/(d'^2 * MF).$$

27. The method of claim 26 wherein the modulation factor is determined by dividing a total dose generated by the radiation system with a delivered dose to the isocenter.

28. The method of claim 14 wherein the accumulated radiation is determined according to the following equation using an averaged modulated field size:

$$L(x, y, z) = L\_TAR(d, \theta) + L\_PS(d', \alpha)$$

wherein L (x, y, z) represents the accumulated leakage, L_TAR(d, θ) represents the first portion of radiation, L_PS(d', α) represents the second portion of radiation, d represents a distance from the POI to the source, θ represents a spatial angle of the POI with respect to the source, d' represents a distance from the POI to the isocenter, α represents a spatial angle of the POI with respect to the isocenter; and wherein the averaged modulated field size is determined by a field size area divided by a modulation factor.

* * * * *